United States Patent [19]

Young et al.

[11] 4,303,657
[45] Dec. 1, 1981

[54] NITROHYDROXYALKYL-SUBSTITUTED QUINOXAXILINE DIOXIDES AND ALKANOIC ACID ESTERS THEREOF

[75] Inventors: Vernon V. Young; Robert D. Williams; Richard E. Ivy, all of Terre Haute, Ind.

[73] Assignee: International Minerals & Chemical Corp., Terre Haute, Ind.

[21] Appl. No.: 40,836

[22] Filed: May 21, 1979

[51] Int. Cl.³ ................ C07D 241/42; C07D 241/52; A61K 31/495
[52] U.S. Cl. .................................. 424/250; 544/353; 426/532
[58] Field of Search ........................ 544/353; 426/532; 424/250

[56] References Cited

U.S. PATENT DOCUMENTS

| | | | |
|---|---|---|---|
| 3,344,022 | 9/1967 | Johnston | 544/353 |
| 3,453,365 | 7/1969 | Lane et al. | 544/353 |
| 3,560,616 | 2/1971 | Shaffer | 424/250 |
| 3,903,281 | 9/1975 | Cox et al. | 544/356 |
| 3,926,992 | 12/1975 | McFarland | 424/250 |

FOREIGN PATENT DOCUMENTS

| | | |
|---|---|---|
| 2312730 | 9/1973 | Fed. Rep. of Germany ...... 544/354 |
| 2730523 | 1/1978 | Fed. Rep. of Germany . |

OTHER PUBLICATIONS

Osumi, Chem. Abs. 81, 145628t (1972).
Lippman, Chem. Abs., 88, 507966 (1977).

*Primary Examiner*—Mark L. Berch
*Attorney, Agent, or Firm*—Robert H. Dewey

[57] ABSTRACT

Nitrohydroxyalkylquinoxaline-1,4-dioxides represented by the formula

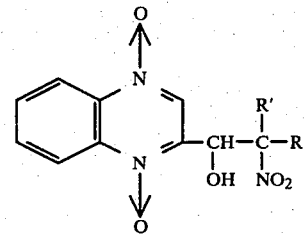

where R is hydrogen, lower alkyl of 1–3 carbon atoms, hydroxymethyl or acetoxymethyl and R' is hydrogen or lower alkyl of 1–2 carbon atoms or R and R' taken together can be alkylene of 5 carbon atoms and alkanoic acid esters thereof. The compounds are useful for promoting growth rate of animals and improving their feed efficiency.

23 Claims, No Drawings

NITROHYDROXYALKYL-SUBSTITUTED QUINOXAXILINE DIOXIDES AND ALKANOIC ACID ESTERS THEREOF

BACKGROUND OF THE INVENTION

This invention relates to substituted quinoxaline-1,4-dioxides. In a particular aspect this invention relates to a method of promoting the growth of animals.

In the business of raising animals for food, it is essential to feed the animals those rations and adjuncts thereto, such as growth promoter stimulants, that provide a rapid weight gain and a high conversion of feed to animal weight. Such compounds cause the animal to gain weight faster during the growth period, thus shortening the time required to bring the animal to market weight. A growth stimulant is a compound which elicits a response of an animal toward its optimum genetic potential from a depression in growth rate and feed efficiency caused by intestinal bacterial flora, stress and subclinical diseases. Some compounds also act to improve feed efficiency, i.e. they permit the animal to gain more weight per unit weight of food than would occur without the compound. Such compounds are highly advantageous in raising animals for food. Antibiotics such as penicillin, bacitracin and tetracyclines have been widely used for this purpose. Antibiotics have several disadvantages, however. There is the possibility that resistant strains of pathogenic organisms may develop. Also, these antibiotics are expensive to use. Accordingly, there is a need for other agents to stimulate the growth of animals.

SUMMARY OF THE INVENTION

It is an object of this invention to provide substituted quinoxaline dioxides.

It is another object of this invention to provide a method for promoting the growth of animals.

It is yet another object of this invention to provide a method for improving the feed efficiency of animals.

Still other objects of this invention will be apparent to those skilled in the art from the disclosure herein.

It is the discovery of this invention to provide nitrohydroxyalkyl-substituted quinoxaline-1,4-dioxides and their alkanoic acid esters and method of preparation. It is also an embodiment of this invention to provide a method of improving the growth rate of animals and increasing their feed efficiency.

DETAILED DISCUSSION

The nitrohydroxyalkyl-substituted quinoxaline-1,4-dioxides of this invention are represented by the formula

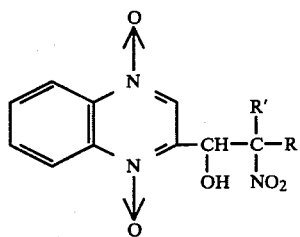

where R is hydrogen, lower alkyl of 1-3 carbon atoms, hydroxymethyl or acetoxymethyl and R' is hydrogen or lower alkyl of 1-2 carbon atoms, or R and R' taken together can be an alkylene group of 5 carbon atoms thereby forming a cyclohexyl moiety. It is also an embodiment of this invention to provide alkanoic acid esters of the hydroxy compounds.

These compounds can be readily esterified, e.g. by reaction with an acid anhydride or acid chloride, and the esters also have the properties of improving growth and increasing the feed efficiency.

The nitrohydroxy compounds of this invention are readily prepared by reacting a nitroalkane of from 1 to 6 carbon atoms with 2-formylquinoxaline-1,4-dioxide hydrate in about a 1:1 mole ratio. It is also an embodiment of this invention to use a nitroalkanoic acid ester or a nitroalkanol in place of the nitroalkane. The nitroalkanes useful in the practice of this invention include but are not limited to nitromethane, nitroethane, 1-nitropropane, 2-nitropropane, 1-nitrobutane, 2-nitrobutane and nitrocyclohexane.

The reaction proceeds readily, especially at elevated temperatures and under alkaline conditions. Advantageously, a lower alkyl alcohol, e.g. of from 1–4 carbon atoms, preferably methanol, is used as a solvent. When a solvent is used, the formyl quinoxaline dioxide hydrate and alkaline agent are preferably heated to near reflux temperatures, then the nitroalkane is added with agitation and the heat source is removed. Agitation is continued until the mixture reaches room temperature, during which time a precipitate forms. It can be recovered by filtration, centrifugation or decantation, and preferably rinsed with a small amount of alkanol solvent, e.g. methanol. In some cases it may be preferable to recover the product by evaporation of the alkyl alcohol. When preferred, the product can be recrystallized from an alcohol solvent.

The formyl quinoxaline dioxide hydrate used in the practice of this invention can be prepared by the acid hydrolysis of 2-formylquinoxaline-1,4-dioxide dimethyl acetal, which is a known compound, described by M. J. Haddadin et al., British Pat. No. 1,305,138. The hydrate compound is readily obtained by dissolving the dimethyl acetal compound in hot dilute hydrochloric acid (1 to 10%). The solution is allowed to cool and is then chilled whereupon the hydrate crystallizes. For a higher purity product, it may be desirable to treat the hot solution with activated charcoal and filtering before crystallization begins.

The alkaline conditions used in the production of the compounds of this invention can be provided by any suitable alkalinizing agent including sodium and potassium hydroxides or alkoxides and alkylamines, but generally strong amines such as tertiary alkylamines, e.g. triethylamine or tributylamine are preferred. The amount can be varied considerably but it should be sufficient to provide, if in an aqueous system, a pH of from about 8 to 11. Generally this can be provided by an amount of, e.g., from 0.01 to 1.0%.

The alkanoic acid esters of the nitrohydroxy compounds of this invention are provided by conventional esterification reaction of the nitrohydroxy compound with an acid chloride or acid anhydride. Preferably, the acid chloride or anhydride is aliphatic of from 2 to 20 carbon atoms. The formic ester can be prepared by reaction with formic acid. The preferred esters are the acetic acid esters.

It is an embodiment of this invention to provide a method for promoting the growth of animals and improving their feed efficiency by administering to them a compound of this invention.

It is contemplated that the method of this invention will be particularly suitable for animals raised for food such as fowl, ruminants, swine and rabbits. Although all members of the fowl family—i.e. chickens, turkeys, geese, ducks, guinea, pheasant and quail—will show increased rate of growth and improved feed efficiency, the method is particularly valuable for chicken broilers and turkeys. Of the ruminants, e.g. cattle, sheep and goats, the method is particularly of value for cattle, e.g. steers.

The method of administration of a compound of this invention is to incorporate it in the feed rations intended for the animal at a concentration of about 50–150 g/ton of feed, preferably about 100 g/ton. The animals are permitted to feed at liberty throughout the growth period. There are many specialized feed rations for different species of animals. The compounds of this invention can be used with any of the known rations.

The term "feed rations" is intended to mean the food provided for the animals, and it is not intended that the invention be limited thereby. Preferably the compound is thoroughly mixed with the feed ration so that it is uniformly dispersed throughout. However, it is also contemplated that it could be sprinkled on the daily food supplies in the form of a powder or as pellets. Thus, it is not intended that the invention be limited to any particular mode of administration.

Any of the known feed rations can be used in the practice of this invention and it is not intended that the invention be limited by the formulation of the ration. Feed rations are formulated to provide the animal for which it is intended with the essential nutrients, minerals, vitamins, bulk, etc. Formulation of these rations are well within the skill of nutritionists.

The invention will be better understood with reference to the following examples. It is understood that these examples are intended for illustration only and it is not intended that the invention be limited thereby.

EXAMPLE 1

2-Formylquinoxaline-1,4-dioxide hydrate 2 g (0.01 mole) was dissolved in 100 ml of warm methanol. Ten drops of triethylamine were added with stirring and 1.3 g of methyl nitroacetate was added incrementally. The heat source was removed and the reaction mixture was allowed to cool to room temperature. The methanol was removed by evaporation and the residue was recrystallized from water, 1 g/75 ml. There was obtained methyl-$\alpha$-nitro-$\beta$-hydroxy-2-quinoxalinepropionate-1,4-dioxide, m.p. 160–162. It was designated P-2229 for convenience. It analyzed as follows:

|  | C | H | N |
|---|---|---|---|
| Calc., %: | 46.61 | 3.59 | 13.59 |
| Found, %: | 47.37 | 3.69 | 13.06 |

Growth promotion and improved feed efficiency were determined as follows:

Two groups of male two-day-old broiler-type chicks were placed into Petersime starter batteries and given feed and water ad libitum for the duration of each test. Each group was subdivided into six sub-groups with ten birds in each sub-group, thus providing sixty birds per group. One group received the basal feed ration, as given in Table 1 and served as a control. The other group receives the same ration, but in addition there was included P-2229 at a concentration of 100 g/ton. The basal ration was a rye diet which alters the microflora of the gut in the bird which results in a growth depressant effect. When a growth stimulant or promotant is added to the diet, the effect on the birds performance will be more apparent than if a corn base diet was used.

The test period was thirteen days. Individual live body weights and pen feed efficiencies were taken at 2 and 14 days of age. The data are given in Table 2. Growth promotion of P-2229 is indicated by the average percentage increase in weight over that of the control group, and feed efficiency is taken as the ratio of weight of feed consumed to weight gained and the increase of this ratio over the ratio exhibited by controls is taken as the increase of feed efficiency.

| Basal Ration | |
|---|---|
| Ground rye | 55.0 |
| Soybean meal 44% | 29.0 |
| Fish solubles 40% | 2.0 |
| Meat and bone meal 50% | 5.0 |
| Dehydrated alfalfa meal | 1.2 |
| Dried whey | 1.0 |
| Fat | 4.0 |
| Dicalcium phosphate 24% ca 18.5% P | 1.0 |
| Livestock mineral 24% ca 6% P | .75 |
| Salt | .50 |
| Vitamin and trace mineral premix | .50 |
| | 100 lbs |
| Analysis | |
| Protein | 23.3% |
| Calcium | 1.03% |
| Phosphorus | 0.84% |
| M.E. kg Calories/lb | 1260 |

The results obtained were as follows:

TABLE 1

| | P-2229 | Control |
|---|---|---|
| Body weight gain, av, g. | 218.75 | 208.73 |
| Increase in weight, % | 4.8 | — |
| Feed efficiency | 1.48 | 1.49 |
| Increase in feed efficiency, % | 0.7 | — |

EXAMPLE 2

The experiment of Example 1 was repeated in all essential details except that nitroethane, 1.5 g (0.02 mole) was substituted for methyl nitroacetate and it was recrystallized from ethanol. There was obtained 2-(1-hydroxy-2-nitropropyl)quinoxaline-1,4-dioxide, m.p. 206–208 with decomposition. It was designated P-2230 for convenience. It analyzed as follows:

| | C | H | N |
|---|---|---|---|
| Calc., %: | 49.81 | 4.18 | 15.85 |
| Found, %: | 50.82 | 4.17 | 15.13 |

The results of the feeding test were as follows:

TABLE 2

| | P-2230 | P-2231 | Control |
|---|---|---|---|
| Body weight gain, av, g. | 222.37 | 221.54 | 208.77 |
| Increase in weight, % | 6.5 | 6.1 | — |
| Feed efficiency | 1.45 | 1.46 | 1.56 |
| Increase in feed efficiency | 7.1 | 6.4 | — |

EXAMPLE 3

The experiment of Example 2 was repeated in all essential details except that nitromethane 1.0 g (0.016 mole) was substituted for nitroethane. There was obtained 2-(1-hydroxy-2-nitroethyl)-quinoxaline-1,4-dioxide, m.p. 202°–204° C., with decomposition. It was designated P-2231 for convenience. It analyzed as follows:

|  | C | H | N |
| --- | --- | --- | --- |
| Calc., %: | 47.81 | 3.16 | 16.73 |
| Found, %: | 47.93 | 3.71 | 16.24 |

The results of the feeding test are given in Table 2.

EXAMPLE 4

The experiment of Example 2 was repeated in all essential details except that 1-nitropropane was substituted for nitroethane in an equimolar amount. There was obtained 2-(1-hydroxy-2-nitrobutyl)quinoxaline-1,4-dioxide, m.p. 197–199. It was designated P-2246 for convenience. It analyzed as follows:

|  | C | H | N |
| --- | --- | --- | --- |
| Calc., %: | 51.61 | 4.69 | 15.05 |
| Found, %: | 52.06 | 4.83 | 14.30 |

The results of the feeding test are given in Table 3.

TABLE 3

|  | P-2246 | P-2265 | Control |
| --- | --- | --- | --- |
| Body weight gain, av, g. | 194.7 | 188.7 | 128.6 |
| Increase in weight, % | 51.4 | 46.7 | — |
| Feed efficiency | 1.54 | 1.59 | 1.82 |
| Increase in feed efficiency | 15.4 | 12.6 | — |

EXAMPLE 5

The experiment of Example 4 was repeated in all essential details except that 2-nitropropane was substituted for 1-nitropropane. There was obtained 2-(1-hydroxy-2-methyl-2-nitropropyl)quinoxaline-1,4-dioxide, m.p. 190–192. It was designated P-2265 for convenience. It analyzed as follows:

|  | C | H | N |
| --- | --- | --- | --- |
| Calc., %: | 51.61 | 4.69 | 15.05 |
| Found, %: | 51.91 | 4.75 | 14.67 |

The results of the feeding tests are given in Table 3.

EXAMPLE 6

The experiment of Example 2 was repeated in all essential details except that 2-nitro-1-butanol was substituted for nitroethane in equimolar amounts. There was obtained 2-(1-hydroxy-2-hydroxymethyl-2-nitrobutyl)-quinoxaline-1,4-dioxide, a viscous liquid. It was designated P-2280 for convenience. It causes improved growth rate and improved efficiency when tested in feed rations. P-2280 is also useful in controlling the growth of certain bacteria and fungi as shown by the following minimum inhibitory concentrations (MIC):

|  | MIC, ug/ml |
| --- | --- |
| *Staphylococcus aureus* | 500–1000 |
| *Streptococcus hemolyticus* | 500–1000 |
| *Escherichia coli* | 100–500 |
| *Pasteurella pseudotuberculosis* | 50–100 |
| *Pseudomonas aeruginosa* | 500–1000 |
| *Shigella dysenteriae* | 500–1000 |
| *Mycobacterium ranae* | 50–100 |
| *Aspergillus niger* | 100–500 |
| *Candida albicans* | 100–500 |
| Pencillium sp. | 100–500 |
| *Aspergillus fumigatus* | 500–1000 |

EXAMPLE 7

A portion of the compound of Example 1, P-2229, was dissolved in an excess of warm acetyl chloride. The mixture was heated to boiling for about 30 minutes, then allowed to cool. The solids which separated were isolated by filtration, rinsed with ether and dried. A sample was purified by recrystallization from a mixture of dimethylsulfoxide and and methanol (1 g/5 ml/45 ml respectively). There was obtained β-acetyl-α-nitro-2-quinoxalinepropionic acid methyl ester-1,4-dioxide. It melted at 155°–158° with decomposition. It was designated P-2236 for convenience. It analyzed as follows:

|  | C | H | N |
| --- | --- | --- | --- |
| Calc., %: | 47.87 | 3.73 | 11.96 |
| Found, %: | 47.67 | 3.75 | 11.13 |

It was tested for growth promotion and ability to improve feed efficiency. The results are given in Table 4.

TABLE 4

|  | P-2236 | Control |
| --- | --- | --- |
| Body weight gain, av., g | 154.92 | 97.33 |
| Increase in weight, % | 59.17 | — |
| Feed efficiency | 1.56 | 1.84 |
| Increase in feed efficiency | 15.2 | — |

EXAMPLE 8

The experiment of Example 7 was repeated in all essential details except that the product of Example 2, P-2230, was substituted for P-2229. There was obtained 2-(1-acetoxy-2-nitropropyl)quinoxaline-1,4-dioxide, m.p. 186–190 with decomposition. It was designated P-2242 for convenience.

It analyzed as follows:

|  | C | H | N |
| --- | --- | --- | --- |
| Calc., %: | 50.81 | 4.26 | 13.68 |
| Found, %: | 51.04 | 4.25 | 13.40 |

The results of the growth test are given in Table 5.

TABLE 5

|  | P-2242 | Control |
| --- | --- | --- |
| Body weight gain, av, g | 210.6 | 165.7 |
| Increase in weight, % | 27.1 | — |
| Feed efficiency | 1.48 | 1.57 |
| Increase in feed efficiency | 5.7 | — |

EXAMPLE 9

The experiment of Example 7 was repeated in all essential details except that the product of Example 3, P-2231 was substituted for P-2229. There was obtained 2-(1-acetoxy-2-nitroethyl)quinoxaline-1,4-dioxide, m.p. 201-204. It was designated P-2243 for convenience. It analyzed as follows:

|  | C | H | N |
|---|---|---|---|
| Calc., %: | 49.15 | 3.78 | 14.33 |
| Found, %: | 48.03 | 3.62 | 12.32 |

The results of the growth test are given in Table 6.

TABLE 6

|  | P-2243 | Control |
|---|---|---|
| Body weight gain, av, g | 240.5 | 144.7 |
| Increase in weight, % | 66.2 | — |
| Feed efficiency | 1.48 | 1.69 |
| Increase in feed efficiency | 12.4 | — |

EXAMPLE 10

The experiment of Example 7 was repeated in all essential details except that P-2246 was substituted for P-2229. There was obtained 2-(1-acetoxy-2-nitrobutyl)-quinoxaline-1,4-dioxide, m.p. 156-158 with decomposition. It was designated P-2277 for convenience. It analyzed as follows:

|  | C | H | N |
|---|---|---|---|
| Calc., %: | 52.33 | 4.71 | 13.08 |
| Found, %: | 52.24 | 4.75 | 12.93 |

P-2277 improves the growth rate and increases the feed efficiency of animals when included in the feed rations.

EXAMPLE 11

The experiment of Example 7 was repeated in all essential details except that P-2265 was substituted for P-2229. There was obtained 2-(1-acetoxy-2-methyl-2-nitropropyl)quinoxaline-1,4-dioxide, m.p. 183-185. It was designated P-2284 for convenience. P-2284 improves the growth rate and increases the feed efficiency of animals when included in the feed rations.

EXAMPLE 12

The experiment of Example 7 is repeated in all essential details except that P-2280 is substituted for P-2229. There is obtained 2-(1-acetoxy-2-acetoxymethyl-2-nitrobutyl)quinoxaline-1,4-dioxide. The compound improves the growth rate and increases the feed efficiency of animals when included in the feed rations.

EXAMPLE 13

The experiment of Example 2 is repeated in all essential details except that 1-nitrobutane is substituted for nitroethane in equimolar amounts. There is obtained 2-(1-hydroxy-2-nitropentyl)quinoxaline-1,4-dioxide. It improves the growth rate and increases the feed efficiency of animals when included in the feed rations.

EXAMPLE 14

The experiment of Example 2 is repeated in all essential details except that 2-nitrobutane is substituted for nitroethane in equimolar amounts. There is obtained 2-(1-hydroxy-2-methyl-2-nitrobutyl)quinoxaline-1,4-dioxide. It improves the growth rate and increases the feed efficiency of animals when included in the feed rations.

EXAMPLE 15

The experiments of Example 2 is repeated in all essential details except that nitrocyclohexane is substituted for nitroethane in equimolar amounts. There is obtained α-(1-nitrocyclohexyl)-2-quinoxalinemethanol-1,4-dioxide. It improves the growth rate and increases the feed efficiency of animals when included in the feed rations.

EXAMPLE 16

The experiment of Example 7 is repeated in all essential details except that the product of Example 13 is substituted for P-2229. There is obtained 2-(1-acetoxy-2-nitropentyl)quinoxaline-1,4-dioxide. It improves the growth rate and increases the feed efficiency of animals when included in the feed rations.

EXAMPLE 17

The experiment of Example 7 is repeated in all essential details except that the product of Example 14 is substituted for P2229. There is obtained 2-(1-acetoxy-2-methyl-2-nitrobutyl)quinoxaline-1,4-dioxide. It improves the growth rate and increases the feed efficiency of animals when included in the feed rations.

EXAMPLE 18

The experiment of Example 7 is repeated in all essential details except that the product of Example 15 is substituted for P-2229. There is obtained the acetic acid ester of the product of Example 15. It improves the growth rate and increases the feed efficiency of animals when included in the feed rations.

We claim:

1. A method of promoting the growth rate of animals comprising administering to them daily in their feed rations a compound of the formula

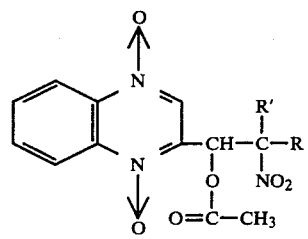

in an amount of from 50 to 150 g/ton of the feed rations, where R is hydrogen, lower alkyl of 1-3 carbon atoms, hydroxymethyl or acetoxymethyl and R' is hydrogen or lower alkyl of 1-2 carbon atoms, or R and R' taken together constitute an alkylene group of 5 carbon atoms.

2. Nitrohydroxyalkylquinoxaline-1,4-dioxides represented by the formula

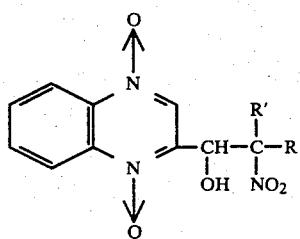

where R is hydrogen, lower alkyl of 1-3 carbon atoms, hydroxymethyl or acetoxymethyl and R' is hydrogen or lower alkyl of 1-2 carbon atoms or R and R' taken together constitute an alkylene group of five carbon atoms.

3. Compounds represented by the formula

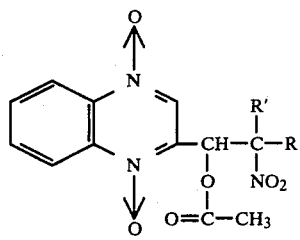

where R is hydrogen, lower alkyl of 1-3 carbon atoms, hydroxymethyl or acetoxymethyl and R' is hydrogen or lower alkyl of 1-2 carbon atoms or R and R' taken together constitute an alkylene group of five carbon atoms.

4. The compounds of claim 2 wherein R and R' are hydrogen.

5. The compounds of claim 2 wherein R is methyl and R' is hydrogen.

6. The compounds of claim 2 wherein R is ethyl and R' is hydrogen.

7. The compounds of claim 2 wherein R is hydroxymethyl and R' is ethyl.

8. The compounds of claim 2 wherein R is acetoxymethyl and R' is hydrogen.

9. The compounds of claim 2 wherein R and R' are methyl.

10. The compounds of claim 2 wherein R is propyl and R' is hydrogen.

11. The compounds of claim 2 wherein R is ethyl and R' is methyl.

12. The compounds of claim 2 wherein R and R' taken together constitute an alkylene group of 5 carbon atoms.

13. The compounds of claim 3 wherein R and R' taken together constitute an alkylene group of five carbon atoms.

14. A method of promoting the growth rate of animals comprising administering to them daily in their feed rations a compound of claim 2 in an amount of from 50 to 150 g/ton of the feed rations.

15. The compounds of claim 3 wherein R is propyl and R' is hydrogen.

16. The compounds of claim 3 wherein R is ethyl and R' is methyl.

17. A feed ration for animals consisting essentially of a nutritional ration containing additionally a compound of claim 2 in an amount of from 5 to 150 g/ton of the feed ration.

18. The compounds of claim 3 wherein R and R' are methyl.

19. The compounds of claim 3 wherein R and R' are hydrogen.

20. The compounds of claim 3 wherein R is methyl and R' is hydrogen.

21. The compounds of claim 3 wherein R is ethyl and R' is hydrogen.

22. The compounds of claim 3 wherein R is hydroxymethyl and R' is ethyl.

23. The compounds of claim 3 wherein R is acetoxymethyl and R' is hydrogen.

* * * * *

UNITED STATES PATENT AND TRADEMARK OFFICE
CERTIFICATE OF CORRECTION

PATENT NO. : 4,303,657
DATED : December 1, 1981
INVENTOR(S) : V. V. Young et al

It is certified that error appears in the above-identified patent and that said Letters Patent are hereby corrected as shown below:

In the title, "QUINOXAXILINE" should read -- QUINOXALINE --

Signed and Sealed this

Eighth Day of June 1982

[SEAL]

Attest:

Attesting Officer

GERALD J. MOSSINGHOFF

Commissioner of Patents and Trademarks